(12) United States Patent
Abt (10) Patent No.: US 11,103,380 B2
(45) Date of Patent: Aug. 31, 2021

(54) AUXILIARY SURGICAL FIELD VISUALIZATION SYSTEM

(71) Applicant: Alcon Inc., Fribourg (CH)

(72) Inventor: Niels Alexander Abt, Winterthur (CH)

(73) Assignee: Alcon Inc.

( * ) Notice: Subject to any disclaimer, the term of this patent is extended or adjusted under 35 U.S.C. 154(b) by 0 days.

(21) Appl. No.: 16/444,523

(22) Filed: Jun. 18, 2019

(65) Prior Publication Data

US 2019/0388271 A1   Dec. 26, 2019

Related U.S. Application Data

(60) Provisional application No. 62/687,362, filed on Jun. 20, 2018.

(51) Int. Cl.
| | |
|---|---|
| *A61F 9/007* | (2006.01) |
| *A61B 3/13* | (2006.01) |
| *A61B 3/14* | (2006.01) |
| *A61F 9/008* | (2006.01) |
| *A61B 3/00* | (2006.01) |
| *G02B 23/12* | (2006.01) |
| *A61B 90/30* | (2016.01) |
| *A61B 90/00* | (2016.01) |

(52) U.S. Cl.
CPC ............ *A61F 9/00736* (2013.01); *A61B 3/13* (2013.01); *A61B 3/145* (2013.01); *A61F 9/008* (2013.01); *A61B 3/0025* (2013.01); *A61B 3/0058* (2013.01); *A61F 2009/00863* (2013.01); *G02B 23/12* (2013.01)

(58) Field of Classification Search
CPC ................. A61F 9/00736; A61F 9/008; A61F 2009/00863; A61B 3/13; A61B 3/145; A61B 3/0025; A61B 3/0058; A61B 3/00; G02B 23/12; G06K 9/00597
See application file for complete search history.

(56) References Cited

U.S. PATENT DOCUMENTS

| | | | | |
|---|---|---|---|---|
| 6,099,522 | A | * | 8/2000 | Knopp ..................... A61B 3/13 606/10 |
| 8,339,447 | B2 | | 12/2012 | Riederer |
| 8,358,330 | B2 | | 1/2013 | Riederer |
| 9,168,173 | B2 | | 10/2015 | Tripathi |
| 2006/0247514 | A1 | * | 11/2006 | Panasyuk ............. A61B 5/0059 600/410 |

(Continued)

FOREIGN PATENT DOCUMENTS

WO         2018109640 A1    6/2018

*Primary Examiner* — Alexander Gee (57) ABSTRACT

An auxiliary surgical field visualization system is described, which includes an auxiliary surgical field camera, configured for acquiring an image of a field of view of a secondary surgical field, wherein the secondary surgical field includes the exterior of a patient's eye undergoing vitreoretinal surgery. The auxiliary surgical field visualization system also includes a display in electronic communication with the auxiliary surgical field camera, wherein the display is configured for receiving, from the auxiliary surgical field camera, a signal that includes the image of the field of view of the secondary surgical field, and upon receiving the signal, displaying the image of the field of view of the secondary surgical field.

11 Claims, 8 Drawing Sheets

(56) References Cited

U.S. PATENT DOCUMENTS

| | | | |
|---|---|---|---|
| 2011/0092984 A1* | 4/2011 | Tripathi | A61B 34/20 606/130 |
| 2012/0130258 A1* | 5/2012 | Taylor | A61B 3/18 600/476 |
| 2013/0088414 A1 | 4/2013 | Artsyukhovich et al. | |
| 2015/0077528 A1* | 3/2015 | Awdeh | A61B 3/14 348/53 |
| 2015/0138504 A1* | 5/2015 | Korb | G01B 11/06 351/206 |
| 2015/0342580 A1* | 12/2015 | Clancy | A61B 10/04 600/567 |
| 2016/0183779 A1* | 6/2016 | Ren | G02B 21/0012 351/206 |
| 2017/0181625 A1* | 6/2017 | Kawakami | A61B 3/0041 |
| 2017/0231711 A1 | 8/2017 | Abt | |
| 2018/0242844 A1* | 8/2018 | Liu | G06T 7/0012 |
| 2018/0271360 A1* | 9/2018 | Barrau | A61B 5/7275 |
| 2018/0332270 A1* | 11/2018 | Hauger | A61B 3/102 |
| 2019/0167074 A1* | 6/2019 | Malinskiy | A61B 1/0638 |
| 2019/0175402 A1 | 6/2019 | Eil et al. | |

\* cited by examiner

AUXILIARY SURGICAL FIELD VISUALIZATION SYSTEM

BACKGROUND

The present disclosure relates to ophthalmic surgery, and more specifically, to an auxiliary surgical field visualization system configured to provide a view of a secondary surgical field that encompasses an area including the exterior of an eye and the surrounding area, during vitreoretinal surgery on the eye.

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others. During vitreoretinal surgery, for example, an ophthalmologist typically uses a surgical microscope to view the fundus through the cornea, while surgical instruments that penetrate the sclera may be introduced to perform any of a variety of different procedures. Typically, during vitreoretinal surgery, the fundus is illuminated using endoillumination, wherein a light source, such as a fiber optic light, is introduced into the internal portion of the eye through the sclera and the surgical microscope provides high magnification imaging of the fundus and other internal structures of the eye during vitreoretinal surgery viewable through the pupil of the eye.

During vitreoretinal surgery, the internal portion of the eye may be considered the primary surgical field. Accordingly, the field of view of the surgical microscope directed toward the endoilluminated internal portion of the eye may be considered the primary surgical field of view. During vitreoretinal surgery, various procedures may take place outside of the primary surgical field of view, such as procedures that take place on or adjacent to the exterior surface of the eye, including manipulation of various instruments, suturing, and so on. Additionally, during vitreoretinal surgery, various surgical components outside of the primary surgical field, such as infusion lines and so on, sometimes require visual inspection, so that it can be verified that the surgical components are performing as required. Existing vitreoretinal surgery systems do not allow the ophthalmic surgeon and others in the operating room to conveniently and quickly view procedures and components outside of the primary surgical field of view. However, development of ophthalmic surgery systems to allow the ophthalmic surgeon and others in the operating room to conveniently and quickly view procedures and components outside of the primary surgical field of view remains challenging.

SUMMARY

The present disclosure relates to an auxiliary surgical field visualization system that includes an auxiliary surgical field camera. The auxiliary surgical field camera is configured for acquiring an image of a field of view of a secondary surgical field, wherein the secondary surgical field includes the exterior of a patient's eye undergoing vitreoretinal surgery. The auxiliary surgical field visualization system also includes a display in electronic communication with the auxiliary surgical field camera, wherein the display is configured for receiving, from the auxiliary surgical field camera, a signal that includes the image of the field of view of the secondary surgical field, and upon receiving the signal, displaying the image of the field of view of the secondary surgical field.

In any of the disclosed implementations, the auxiliary surgical field visualization system may further include the following details, which may be combined with the above system and with one another in any combinations unless clearly mutually exclusive:

(i) the eye may be illuminated using endoillumination;

(ii) the secondary surgical field may have a light intensity of less than 2000 lux;

(iii) the auxiliary surgical field camera may be an infra-red camera, a low-light camera, or a night vision camera;

(iv) the area of the field of view of the secondary surgical field may be between about 3 $cm^2$ and 36 $cm^2$;

(v) the image may be a real-time image;

(vi) the display may be further configured to receive, from a primary surgical field camera configured for acquiring an image of a field of view of a primary surgical field including an internal view of a patient's eye undergoing vitreoretinal surgery, a signal that includes the image of the field of view of the primary surgical field, and displaying the image of the field of view of the primary surgical field;

(vii) the display may be configured for simultaneously displaying the image of the field of view of the secondary surgical field and the field of view of the primary surgical field;

(viii) the display may be a standard definition (SD) display, a high definition (HD) display, a cathode ray tube (CRT) display, a projection screen display, a liquid crystal display (LCD), an organic light emitting diode (OLED) display, a plasma display, a light emitting diodes (LED) display, or a 3-dimensional (3D) display;

(ix) the auxiliary surgical field visualization system may include an NGENUITY® 3D Visualization System;

(x) the auxiliary surgical field visualization system may include a processor and a non-transitory computer-readable medium accessible by the processor, wherein the non-transitory computer readable medium contains instructions executable by the processor for receiving, from the auxiliary surgical field camera, a signal that includes the image of the field of view of the secondary surgical field, and upon receiving the signal, sending the signal to the display;

(xi) the non-transitory computer-readable medium may include instructions executable by the processor for receiving, from a primary surgical field camera configured for acquiring an image of a field of view of a primary surgical field comprising an internal view of a patient's eye undergoing vitreoretinal surgery, a signal that includes the image of the field of view of the primary surgical field, and upon receiving the signal, sending the signal to the display;

(xii) the auxiliary surgical field visualization system may allow visualization on a display of one or more secondary surgical manipulations, wherein the secondary surgical manipulations are directed to a site on or adjacent to the exterior surface of the eye;

(xiii) the secondary surgical manipulations may include one or more manipulations selected from inserting an instrument into the eye through a trocar cannula, suturing an exterior surface of the eye, placing a trocar cannula, removing a trocar cannula, inspecting a function of a surgical component, retrieving a foreign body, placing indentors or muscle hooks, using cryo-probes, placing scleral buckles and encircling bands, and placing a direct or an indirect contact lens;

(xiv) the auxiliary vitreoretinal surgery visualization system may allow visualization on a display of one or more surgical components in the secondary surgical field;

(xv) the surgical components in the secondary surgical field may be selected from a trocar cannula, an infusion line, a needle holder, an indentor, a muscle hook, an instrument tip prior to insertion trough a trocar cannula, a flexible iris retractor, a direct or indirect contact lens, and a needle and suture; and (xvi) the display may be viewable by a plurality of individuals.

BRIEF DESCRIPTION OF THE DRAWINGS

For a more complete understanding of the present invention and its features and advantages, reference is now made to the following description, taken in conjunction with the accompanying drawings, which are not to scale, and in which.

DETAILED DESCRIPTION

In the following description, details are set forth by way of example to facilitate discussion of the disclosed subject matter. It should be apparent to a person of ordinary skill in the art, however, that the disclosed embodiments are exemplary and not exhaustive of all possible embodiments.

The present disclosure relates to ophthalmic surgery, and more specifically, to an auxiliary surgical field visualization system configured to provide a view of a secondary surgical field that encompasses an area including the exterior of the eye and the surrounding area, during vitreoretinal surgery.

Figure 1:
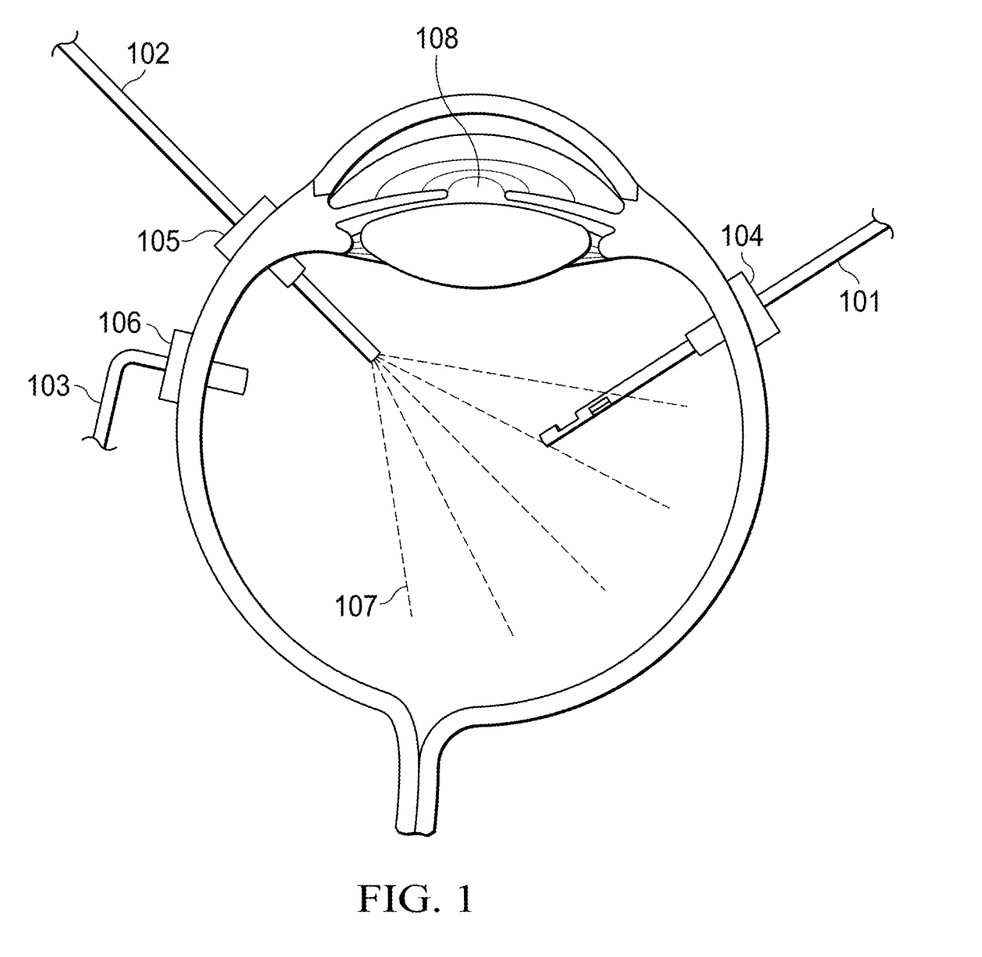
FIG. 1 is an exemplary schematic showing a side view of an eye undergoing a vitreoretinal surgical procedure.

For example, FIG. 1 is an exemplary schematic showing a side view of an eye undergoing a vitreoretinal surgical procedure. Indicated in the schematic diagram are various tools inserted into the eye, including a vitrector cutting device 101 that removes the eye's vitreous gel in a slow, controlled fashion. Also shown is a light pipe 102, which provides illumination inside the eye, referred to as endoillumination. Also shown is an infusion cannula 103, used to replace fluid in the eye with a saline solution and to maintain proper eye pressure. The vitrector cutting device 101, the infusion cannula 102, and the light pipe 103 are typically inserted into the eye through respective trocar cannulas 104, 105 and 106 that are inserted into incisions in the sclera following a procedure using a trocar cannula system, as would be understood by skilled persons. During a vitreoretinal surgery, such as shown in the exemplary schematic diagram in FIG. 1, the ophthalmic surgeon visualizes the illuminated portion of the fundus 107 using a microscope directed to view the internal part of the eye through the pupil 108.

Figure 2:
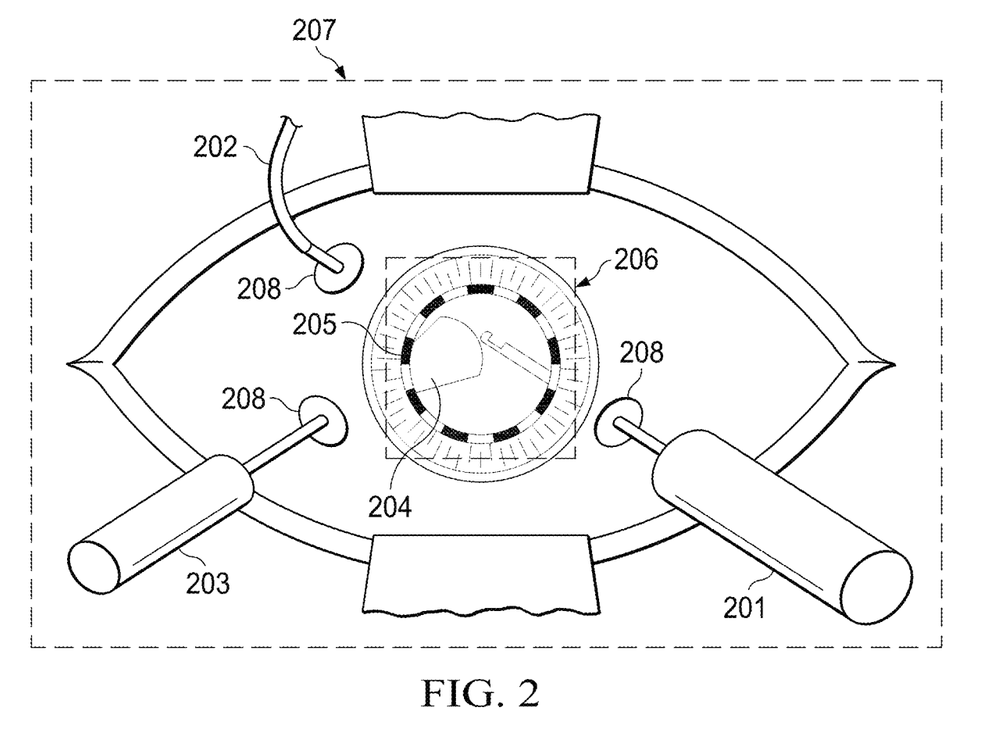
FIG. 2 is an exemplary schematic showing a top-down view of an eye undergoing a vitreoretinal surgical procedure.

FIG. 2 is a schematic showing an exemplary top-down view, corresponding to an en face view of an eye undergoing an exemplary vitreoretinal surgical procedure, similar to the exemplary procedure shown in side-view in FIG. 1. Indicated in the schematic diagram are various tools inserted into the eye through trocar cannulas 208, including a vitrector cutting device 201, an infusion cannula 202, and a light pipe 203. During a vitreoretinal surgery, such as shown in the exemplary schematic diagram in FIG. 2, the ophthalmic surgeon visualizes the endoilluminated portion of the fundus 204 using a microscope directed to view the internal part of the eye through the pupil 205.

Typically, during vitreoretinal surgery, the ophthalmic surgeon views the endoilluminated portion of the eye at high magnification. Accordingly, at high magnification, the region of the eye viewable during surgical manipulations involving the endoilluminated internal portion of the eye encompasses a relatively small area of the en face view of the eye, for example as shown by a dashed line box indicating a view of the primary surgical field 206 in FIG. 2.

Also shown in FIG. 2 is a dashed line box indicating a secondary surgical field 207. The term "secondary surgical field" as used herein refers to a region that generally encompasses an area including the exterior surface of the eye and the surrounding area, during vitreoretinal surgery. Accordingly, the secondary surgical field encompasses a region including an exterior portion of the eye and the surrounding area, in which various surgical manipulations may take place during vitreoretinal surgery, and may include, but are not limited to, the externally viewable features of the eye, for example including externally viewable portions of the pupil, iris, cornea, sclera, vessels, and incision sites, e.g., within the sclera, and also may include facial structures surrounding the eye that may be viewable during ophthalmic surgery such as eyelids, eyelashes, eyebrow, nose, cheeks, and so on. The secondary surgical field may also include various externally viewable surgical components such as surgical tools, instruments, tubing, clamps, infusion cannulas, light pipes, vitrector cutting devices, trocar cannulas, cue-tips, drapes, speculum, visualization apparatus e.g. BIOM® (Oculus Optikgeräte GmbH, Wetzlar-Dutenhof, Germany), direct or indirect contact lenses, IOL, injectors, cutting devices, needle holders, indentors, muscle hooks, instrument tips prior to insertion trough a trocar cannula, flexible iris retractors, needles and sutures and other objects identifiable by skilled persons, that may be used during ophthalmic surgery, that may be introduced into the general external area of the eye undergoing surgery. The term "externally viewable" in general indicates something that is viewable within the secondary surgical field, such as something that is exterior to the eye, or on or near the exterior surface of the eye. In particular, the term externally viewable refers to something that may not be viewable within the primary surgical field, such as the various features of the eye and surrounding facial features and surgical instruments described herein. The term secondary surgical field includes the exterior portion of the eye that is not typically viewable using endoillumination. Accordingly, the term secondary surgical field as used herein generally refers to a surgical field that is supplementary, auxiliary, or additional to the primary surgical field, generally including a spatial region that includes the external portion of the eye and the area surrounding the eye, or adjacent to the eye, during vitreoretinal surgery.

It will be apparent to skilled persons that the secondary surgical field is generally larger than the primary surgical field, and may encompass an approximately en face area when viewed top-down, for example as shown in FIG. 2, between, or between about, 1 $cm^2$ and 36 $cm^2$, for example an area encompassing approximately a square area of between, or about between, e.g., 1 cm×1 cm, and e.g. 6 $cm^2$×6 $cm^2$, although other shapes are possible, such as rectangular areas. The angle of the 2-dimensional plane of the en face area of the external surgical field may be the same, or may be different, to the angle of the 2-dimensional plane of the en face area of the primary surgical field.

In general, surgical procedures described herein include primary surgical manipulations and secondary surgical manipulations. The term "primary surgical manipulations" refers to surgical manipulations that are viewable at high magnification in the primary surgical field, such as manipulations that target the interior of the endoilluminated eye. In contrast, the term "secondary surgical manipulations" refers to surgical manipulations that may be viewable at lower magnification and may be performed in the secondary surgical field, such as manipulations that generally target the exterior portion of the eye or are viewable taking place on or adjacent to, or in close proximity to (e.g., within about 5 cm) of an exterior surface of the eye.

For example, secondary surgical manipulations include procedures such as manipulation of various instruments, suturing, and so on, that take place on or near the exterior portion of the eye. In particular, for example, during vitreoretinal surgery, insertion of instruments through trocar cannulas requires visualization of the insertion location on the outside of the eye, such that the cannula hub and the instrument tip needs to be visualized for successful introduction. This requires visualization at lower magnification, or of a larger field of view, and/or on a different focal plane, than is used for viewing primary surgical manipulations that target structures inside the eye.

Additionally, during vitreoretinal surgery, visual inspection of portions of various surgical components in the secondary surgical field, such as infusion lines and so on, may be required from time to time, so that it can be verified that the surgical components are performing as required. Visual inspection of the components may also require lower magnification, or of a larger field of view, and/or a different focal plane, than is used for viewing primary surgical manipulations that target structures inside the eye.

Additionally, as would be understood by skilled persons, when using endoillumination, external microscopy illumination light sources, such as a microscope light source external to the eye, are typically turned off, so that the illuminated interior portion of the eye viewable through the pupil of the endoilluminated eye is contrasted against a predominantly dark, or relatively non-illuminated exterior portion of the endoilluminated eye. For example, when using the exemplary NGENUITY® 3D Visualization System for performing vitreoretinal surgery, the interior of the eye is visualized by endoillumination, and external light sources are typically turned off.

Accordingly, vitreoretinal surgery procedures that use endoillumination typically take place in a darkened operating room or generally take place wherein the secondary surgical field is relatively dark. As would be understood by skilled persons, having a darkened operating room or a relatively dark secondary surgical field during vitreoretinal surgery is useful for increased contrast of the endoilluminated image and reducing unwanted glare and glistening from the endoilluminated image. However, having a dark operating room or an otherwise relatively dark secondary surgical field makes it difficult to adequately visualize the secondary surgical field, and therefore makes it difficult to perform secondary surgical manipulations and visual inspections of components in the secondary surgical field in absence of illumination of the secondary surgical field. The terms "darkened" or "relatively dark" as used herein refer to light levels that are below, or about below, 2000 lux.

Accordingly, previous approaches for viewing the secondary surgical field during vitreoretinal surgery typically involve turning on a light source external to the eye, in order to illuminate the secondary surgical field for viewing.

In addition, one previous approach for visualizing the secondary surgical field involves zooming out the field of view and/or adjusting the focal plane of the surgical microscope from the primary surgical field to allow visualization of the secondary surgical field using the surgical microscope. Using this approach, after performing exterior surgical manipulations and/or visual inspections in the external surgical field, the surgical microscope must be zoomed in again and/or refocused so that the surgical microscope's field of view is again directed to the primary surgical field, and the external illumination turned off. It will be apparent to skilled persons that this previous approach has disadvantages, as it is cumbersome and interrupts the surgical procedure, as it requires time and readjustment of the microscope, which lengthens the time required for surgery.

As an alternative to zooming out the surgical microscope field of view, another previous approach for viewing the external surgical field during vitreoretinal surgery involves the use of an auxiliary optical lens such as a loupe or magnifying glass, or an auxiliary set of lower magnification eyepieces, configured to provide the ophthalmic surgeon with an overview of the secondary surgical field. For example, one previous approach uses an auxiliary magnifying glass or loupe additionally attached to the housing of the surgical microscope near the surgical microscope oculars. This previous approach also has disadvantages. For example, using such an approach the external field viewable through such auxiliary optics is only viewable by the ophthalmic surgeon, and is not simultaneously viewable by other personnel in the operating room. Additionally, use of auxiliary optical magnifying glasses or auxiliary eyepieces also typically requires that external lights be turned on to adequately illuminate the external surgical field for viewing.

Described herein is an auxiliary surgical field visualization system that may be used during ophthalmic surgery, such as vitreoretinal surgery, to allow the ophthalmic surgeon, and others in the operating room, to conveniently view the secondary surgical field thereby conveniently allowing visualization of secondary surgical manipulations and performance of visual checks of components outside of the primary surgical field of view.

In particular, upon reading of the present disclosure, it will be apparent to skilled persons that the auxiliary surgical field visualization system described herein has various advantages over previous approaches in that it allows, for example, various secondary surgical manipulations and visual checks in the secondary surgical field to be performed without the need to refocus the field of view of the surgical microscope away from the primary surgical field. Accordingly, the surgical microscope can remain focused on the primary surgical field. In addition, the auxiliary surgical field visualization system described herein allows the ophthalmic surgeon and others in a surgical team in the operating room, such as nurses and technicians, to simultaneously view the external surgical field, which allows the surgical team to have improved understanding of the surgical procedure in process, improved communication and improved workflow between members of the surgical team.

Figure 3A:
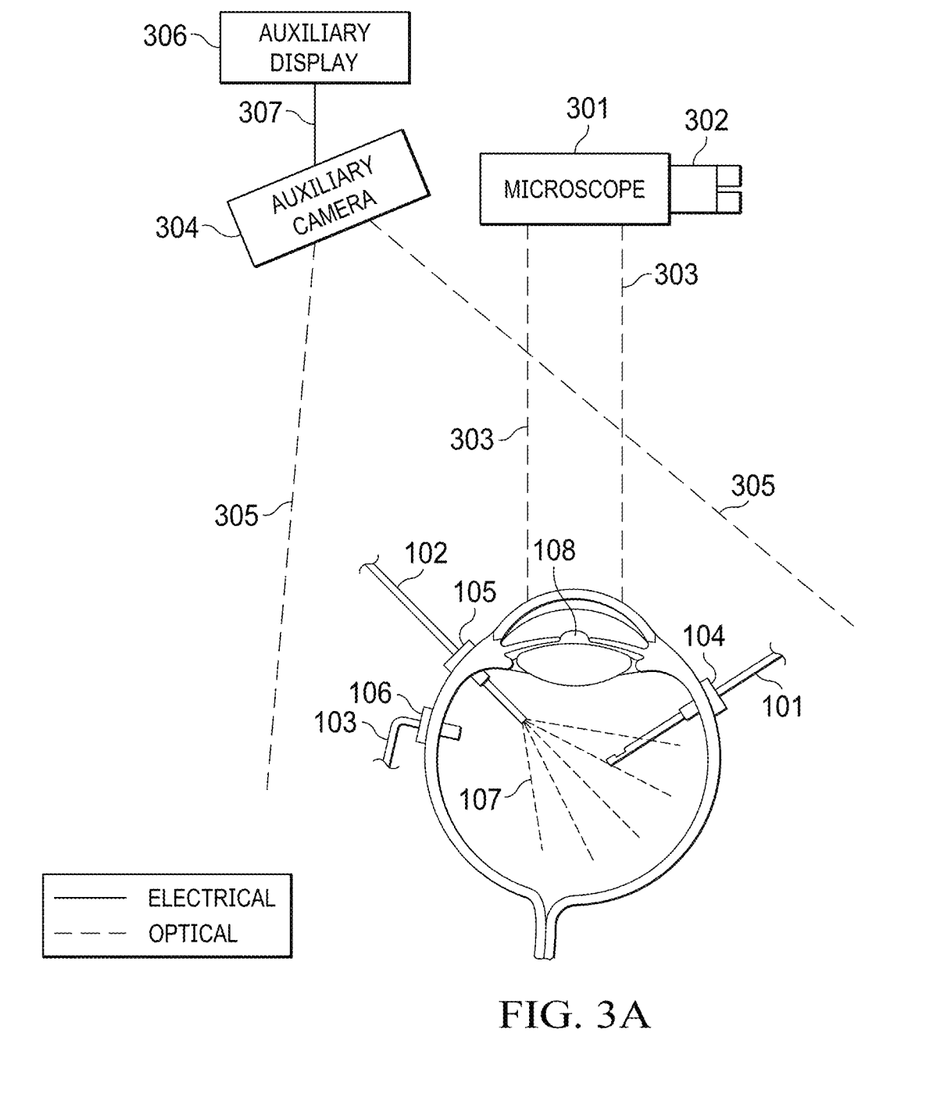
FIG. 3A is a schematic showing an exemplary auxiliary surgical field visualization system.

FIG. 3A is a schematic showing an implementation of an exemplary auxiliary surgical field visualization system. Shown in FIG. 3A is a side-view of an eye undergoing a vitreoretinal surgical procedure as shown in FIG. 1, including various tools inserted into the eye, including the vitrector cutting device 101, the light pipe 102, and the infusion cannula 103, inserted into the eye through respective trocar cannulas 104, 105 and 106. In FIG. 3A, the primary surgical field including the illuminated portion of the fundus 107 and other internal structures of the eye are viewed through the pupil 108 using a surgical microscope 301, for example having eyepieces 302. Dashed lines 303 indicate exemplary boundaries of the field of view of the primary surgical field as viewed by the surgical microscope 301. The auxiliary surgical field visualization system includes an auxiliary camera 304. The auxiliary surgical field camera is configured for acquiring an image of a field of view of a secondary surgical field, wherein the secondary surgical field includes the exterior of a patient's eye undergoing vitreoretinal surgery. Dashed lines 305 indicate exemplary boundaries of the field of view of the secondary surgical field. A display, referred to as an auxiliary display 306, in electronic communication 307 with the auxiliary surgical field camera 304, is configured for receiving, from the auxiliary surgical field camera 304, a signal that includes the image of the field of view of the secondary surgical field, and upon receiving the signal, displaying the image of the field of view of the secondary surgical field. Solid lines 307 herein indicate electronic or electrical communication and may in various implementations be wired or wireless communication. Dashed lines 303 and 305 herein indicate exemplary boundaries of an optical field of view respectively of a primary surgical field and a secondary surgical field.

The term "camera" as used herein refers to a device that includes a photosensor. A photosensor is an electromagnetic sensor that responds to light and produces or converts it to an electrical signal which can be transmitted to a receiver for signal processing or other operations and ultimately read or viewed by an instrument or an observer.

Accordingly, a camera is a device used to capture images, either as still photographs or as sequences of moving images (movies or videos). A camera generally consists of an enclosed hollow with an opening (aperture) at one end for light to enter, and a recording or viewing surface for capturing the light at the other end. The recording surface can be chemical, as with film, or electronic. Cameras can have a lens positioned in front of the camera's opening to gather the incoming light and focus all or part of the image on the recording surface. The diameter of the aperture is often controlled by a diaphragm mechanism, but alternatively, where appropriate, cameras have a fixed-size aperture.

Exemplary electronic photosensors in accordance with the present disclosure include, but are not limited to, complementary metal-oxide-semiconductor (CMOS) sensors or charge-coupled device (CCD) sensors. Both types of sensors perform the function of capturing light and converting it into electrical signals. A CCD is an analog device. When light strikes the CCD it is held as a small electrical charge. The charges are converted to voltage one pixel at a time as they are read from the CCD. A CMOS chip is a type of active pixel sensor made using the CMOS semiconductor process. Electronic circuitry generally located next to each photosensor converts the received light energy into an electrical voltage and additional circuitry then converts the voltage to digital data which can be transmitted or recorded.

The real-time video signal transmitted can be a digital video signal which is a digital representation of discrete-time signals. Often times, digital signals are derived from analog signals. As would be understood by persons skilled in the art, a discrete-time signal is a sampled version of an analog signal where the value of the datum is noted at fixed intervals (for example, every microsecond) rather than noted continuously. Where the individual time values of the discrete-time signal, instead of being measured precisely (which would require an infinite number of digits), are approximated to a certain precision—which, therefore, only requires a specific number of digits—then the resultant data stream is termed a "digital" signal. The process of approximating the precise value within a fixed number of digits, or bits, is called quantization. Thus, a digital signal is a quantized discrete-time signal, which in turn is a sampled analog signal. Digital signals can be represented as binary numbers, so their precision of quantization is measured in bits.

It will be appreciated by those of ordinary skill in the art that the auxiliary surgical field camera described herein includes, in some implementations, a camera configured to acquire an image corresponding to an optical view of a secondary surgical field and transmit that information as a real-time video signal that can be recorded or presented for display and viewing.

In some implementations, the transmitted digital video signal is capable of producing an image having a suitable resolution, such as a resolution of at least about 1280 lines by 720 lines. This resolution corresponds to the typically minimum resolution for what one of ordinary skill in the art would consider to be high definition or an HD signal. Other suitable resolutions are also contemplated, such as standard resolution, e.g. 640 lines by 480 lines, and so on.

"Real-time" as used herein generally refers to the updating of information at the same rate as data is received. More specifically, in the context of the present invention "real-time" means that the image data is acquired, processed, and transmitted from the photosensor at a high enough data rate and a low enough delay that when the data is displayed objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $1/30^{th}$ second of delay.

In the auxiliary surgical field visualization system described herein, the video signal is received and presented on a video display having corresponding resolution capabilities. Exemplary visual displays include cathode ray tubes, projection screens, liquid crystal displays, organic light emitting diode displays, plasma display panels and light emitting diode displays, among others identifiable by skilled persons.

The auxiliary camera can be either a conventional camera or a 3D camera with two lenses. The auxiliary camera described herein may in some implementations include stereoscopic lenses configured to provide a stereoscopic 3-dimensional image. When the real-time video signal described herein includes multiple views of the target object or tissue the video display can be made three dimensional ("3D") so that depth of field is presented to the ophthalmic surgeon. Exemplary types of high resolution 3D video displays include stereoscopic 3D displays using polarized glasses such as those developed by TrueVision Systems, Inc. Alternatively, autostereoscopic 3D displays that do not require the use of any special glasses or other head gear to direct different images to each eye can be used. Similarly, holographic 3D displays are also contemplated as being within the scope of the present disclosure.

The auxiliary surgical field camera may have one or more lenses configured to provide a suitable magnification of the external surgical field. For example, one or more lenses configured to provide a magnification between, or between about, 1× to 10× may be used in the auxiliary surgical field camera. For example, the magnification may be between, or between about, 1×-1.5×, 1.5-2×, 2×-2.5×, 2.5×-3×, 3×-3.5×, 3.5×-4×, 4×-4.5×, 4.5×-5×, 5×-5.5×, 5.5×-6×, 6×-6.5×, 6.5×-7×, 7×-7.5×, 7.5×-8×, 8×-8.5×, 8.5×-9×, 9×-9.5×, or 9.5×-10×.

As will be understood by skilled persons, the magnification level typically employed by the auxiliary surgical field camera will be relatively lower than the high magnification used by the surgical microscope for viewing the primary surgical field. The term "high magnification" as used herein may refer to any value or range of magnification that may be typically used for visualization of primary surgical manipulations during ophthalmic surgery, such as vitreoretinal surgery, identifiable by skilled persons. For example, in some implementations, an exemplary high magnification may refer to a magnification value within a range of about 2× to 100×, or about 10× to 40×, or about 10× to 20×, among other ranges identifiable by skilled persons. In some implementations, high magnification may refer to a magnification value of about 5× to 20×, 10× to 15×, or 10×, 15× or 20×.

The magnification of a particular auxiliary surgical field visualization system, or a surgical microscope, may be calculated by taking into account factors of lenses, such as the focal length, and the magnification factor set on the zoom components of the system, among other factors identifiable by skilled persons. Methods and systems that include components having optical and/or digital zoom capability are contemplated in the present disclosure.

The photosensor of a camera may be capable of responding to or detecting any or all of the wavelengths of light that form the electromagnetic spectrum. Alternatively, the photosensor may be particularly sensitive to a more restricted range of wavelengths. In particular, in some implementations described herein, because vitreoretinal surgery is typically performed in a darkened operating room, the auxiliary surgical field camera described herein may include a photosensor suitable for capturing an infrared image, a low light image, or a night vision image.

As would be understood by skilled persons, the term "infrared camera", otherwise known as a thermographic camera or a thermal imaging camera, is a device that forms an image using infrared radiation, similar to a common camera that forms an image using visible light. Infrared wavelengths extend from the nominal red edge of the visible spectrum at 700 nanometers (frequency 430 THz), to 1 millimeter (300 GHz). Instead of the typical 400-700 nm range of the visible light camera, infrared cameras may typically operate in wavelengths as long as 14,000 nm (14 µm). Lenses used in infrared cameras are typically made from materials such germanium or sapphire crystals rather than glass, as glass blocks long-wave infrared light. Images from infrared cameras may be monochrome or pseudo-colored. Thermographic cameras can be broadly divided into two types: those with cooled infrared image detectors and those with uncooled detectors. Cooled detectors are typically contained in a vacuum-sealed case or dewar and cryogenically cooled. The cooling is typically necessary for the operation of the semiconductor materials used. Materials used for cooled infrared detection include photodetectors based on a wide range of narrow gap semiconductors including indium antimonide (3-5 µm), indium arsenide, mercury cadmium telluride (MCT) (1-2 µm, 3-5 µm, 8-12 µm), lead sulfide, and lead selenide. Infrared photodetectors can be created with structures of high band gap semiconductors such as in Quantum well infrared photodetectors. Uncooled thermal cameras use a sensor operating at ambient temperature, or a sensor stabilized at a temperature close to ambient using small temperature control elements. Modern uncooled detectors typically use sensors that work by the change of resistance, voltage or current when heated by infrared radiation. These changes are then measured and compared to the values at the operating temperature of the sensor. Uncooled detectors are mostly based on pyroelectric and ferroelectric materials or microbolometer technology. The materials are used to form pixels with highly temperature-dependent properties, which are thermally insulated from the environment and read electronically. Ferroelectric detectors operate close to phase transition temperature of the sensor material; the pixel temperature is read as the highly temperature-dependent polarization charge. Silicon microbolometers include a layer of amorphous silicon, or a thin film vanadium oxide sensing element suspended on silicon nitride bridge above the silicon-based scanning electronics. Materials used for the uncooled focal plane sensor arrays include amorphous silicon (a-Si), vanadium (V) oxide (VOx), lanthanum barium manganite (LBMO), lead zirconate titanate (PZT), lanthanum doped lead zirconate titanate (PLZT), lead scandium tantalate (PST), lead lanthanum titanate (PLT), lead titanate (PT), lead zinc niobate (PZN), lead strontium titanate (PSrT), barium strontium titanate (BST), barium titanate (BT), antimony sulfoiodide (SbSI), and polyvinylidene difluoride (PVDF), among others identifiable by skilled persons. Examples of commercially available infrared cameras include thermography cameras available from vendors such as FLIR and FLUKE, among others identifiable by skilled persons.

The term "low light camera" as used herein refers to a camera that may have a wide aperture lens allowing more photons to hit the photosensor and/or a photosensor with increased sensitivity. As would be understood by skilled persons, the lens aperture is usually specified as an f-number, the ratio of focal length to effective aperture diameter. A lens typically has a set of marked "f-stops" that the f-number can be set to. A lower f-number denotes a greater aperture opening which allows more light to reach the film or image sensor. The photography term "one f-stop" refers to a factor of √2 (approx. 1.41) change in f-number, which in turn corresponds to a factor of 2 change in light intensity. For example, typical ranges of apertures used in cameras are about f/2.8-f/22 or f/2-f/16, covering 6 stops, which may for example be divided into wide, middle, and narrow of 2 stops each, approximately f/2-f/4, f/4-f/8, and f/8-f/16 or (for a slower lens) f/2.8-f/5.6, f/5.6-f/11, and f/11-f/22. High sensitivity photosensors are typically designed with large pixels so that they have a large area to collect light. Photosensors used in low light cameras also typically have high quantum efficiency for converting light photons to electrons. High sensitivity sensors include, for example, doped silicon sensors for optimal photon conversion of light wavelengths in the visible light spectrum. Some low light cameras use frame transfer or full frame sensors and so use the full pixel area for light collection. Other low light cameras include a microlens located over every pixel to collect light from a larger area and focus it onto the smaller light collecting pixel area.

The term "night vision" can be broadly divided into three main categories: image intensification, active illumination and thermal imaging. For example, an image intensifier may refer to a vacuum tube device for increasing the intensity of available light to allow use under low-light conditions, or for conversion of non-visible light sources, such as near-infrared or short wave infrared to visible. Image intensifiers typically operate by converting photons of light into electrons, amplifying the electrons (e.g., with a microchannel plate), and then converting the amplified electrons back into photons for viewing. For example, image intensifiers are used in devices such as night vision goggles. In image intensifiers, when light strikes a charged photocathode plate, electrons are emitted through a vacuum tube that strike the microchannel plate that cause the image screen to illuminate with a picture in the same pattern as the light that strikes the photocathode, and is on a frequency that the human eye can see. Active illumination couples imaging intensification technology with an active source of illumination in the near infrared (NIR) or shortwave infrared (SWIR) band. Examples of such technologies include various low light cameras. Active infrared night-vision typically combines infrared illumination of spectral range 700-1,000 nm (just below the visible spectrum of the human eye) with CCD cameras sensitive to this light. The resulting image is typically displayed in monochrome. Laser range gated imaging is another form of active night vision which utilizes a high powered pulsed light source for illumination and imaging. Range gating is a technique which controls the laser pulses in conjunction with the shutter speed of the camera's detectors. Gated imaging technology can be divided into single shot, where the detector captures the image from a single light pulse, and multi-shot, where the detector integrates the light pulses from multiple shots to form an image.

During ophthalmic surgery, because of the small size and delicate nature of the eye structures, surgeons typically use a microscope to magnify visualization of a patient's eye or a part of the eye that is being operated on. Typically, in the past, during ophthalmic surgery, surgeons used eyepieces, otherwise known as oculars, to view the eye or part thereof that is being magnified by the microscope. During ophthalmic surgery, stereo microscopes having two eyepieces viewable by both eyes simultaneously for binocular view are typically used. Some ophthalmic surgery procedures can take several hours to perform, and therefore previously, during ophthalmic surgery, ophthalmic surgeons would often be required to look through the binocular eyepieces of their microscopes for hours on end.

More recently, as an alternative to using eyepieces, or in addition, during ophthalmic surgery, developments in digital microscopy have allowed an image of the eye or part thereof that is magnified by the microscope to be displayed on a screen viewable by the surgeon and other personnel in an operating room. Among the benefits of using a display screen, rather than using microscope oculars, to visualize eye structures during ophthalmic surgery include decreased fatigue and increased comfort for the surgeon. In addition, unlike microscopes oculars, because the display can be viewed by more than one person at a time, the use of a display is useful for teaching and improves communication regarding the surgical procedure between personnel in the operating room.

Figure 3B:
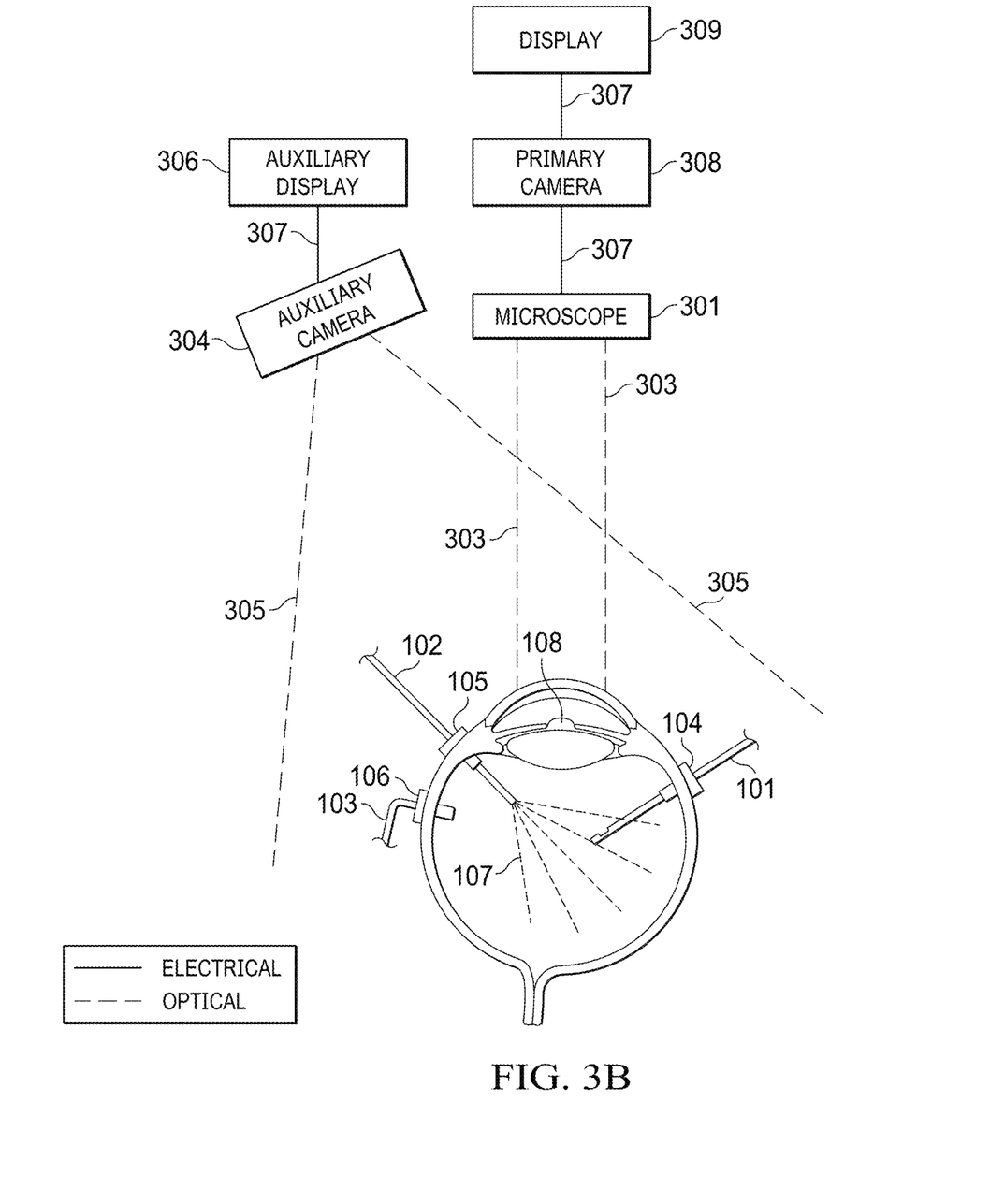
FIG. 3B is another schematic showing an exemplary auxiliary surgical field visualization system.

FIG. 3B is a schematic showing another implementation of an exemplary auxiliary surgical field visualization system. As in FIG. 3A, the auxiliary surgical field visualization system includes an auxiliary camera 304 configured for acquiring an image of a field of view of the secondary surgical field, shown by dashed lines 305 indicating exemplary boundaries of the field of view of the secondary surgical field. An auxiliary display 306, in electronic communication 307 with the auxiliary surgical field camera 304, is configured for receiving, from the auxiliary surgical field camera 304, a signal comprising the image of the field of view of the secondary surgical field, and upon receiving the signal, displaying the image of the field of view of the secondary surgical field. In contrast to the exemplary implementation shown in FIG. 3A, the exemplary implementation shown in FIG. 3B includes a digital surgical microscope 301 in electronic communication 307 with a digital primary camera 308 configured for capturing an image of the primary surgical field indicated by dashed lines 303. In FIG. 3B, a display 309 receives a signal from the primary camera 308. Accordingly, the exemplary auxiliary surgical field visualization system shown in FIG. 3B has a separate auxiliary display 306 to the display 309 used for displaying the magnified image of the primary surgical field 303.

Ophthalmic surgery visualization platforms utilizing digital microscopy and display screens applicable to various implementations of the system described herein generally include at least one high resolution photosensor such as a camera or charge coupled device (CCD) which is capable of receiving and acquiring a plurality of optical views of an eye under magnification by a microscope. Those skilled in the art will appreciate that receiving light in visible wavelengths in addition to wavelengths outside of the wavelengths of normal visible light is also within the scope of the present disclosure. In general, the high resolution photosensor then transmits a resultant real-time high-resolution video signal which is transmitted, either directly or via a processor executing instructions contained in a non-transitory computer readable medium, to at least one high resolution video display. In some configurations, because of the multiple high resolution optical views transmitted and presented on the display, the operator of the visualization platform, or others, is able to view a real-time high definition three-dimensional visual image of the target object or tissue.

Exemplary real-time visualization platforms suitable for implementing the system described herein include those described U.S. Pat. Nos. 9,168,173, 8,339,447, and 8,358,330, all of which are hereby incorporated by reference.

The term "display" as used herein refer to any device capable of displaying a still or video image. Preferably, the displays of the present disclosure display high definition (HD) still images and video images or videos which provide a surgeon with a greater level of detail than a standard definition (SD) signal. In some implementations, the displays present such HD stills and images in three dimensions (3D). Exemplary displays include HD monitors, cathode ray tubes, projection screens, liquid crystal displays, organic light emitting diode displays, plasma display panels, light emitting diodes (LED) or organic LED (OLED), 3D equivalents thereof and the like. 3D HD holographic display systems are considered to be within the scope of the present disclosure.

Examples of systems for digital microscopy that utilizes display screens for visualization during ophthalmic surgery include Alcon Laboratories NGENUITY® 3D Visualization System (Alcon, Inc. Corporation Switzerland, Hunenberg Switzerland), a platform for Digitally Assisted Vitreoretinal Surgery (DAVS). The NGENUITY® 3D Visualization System allows retinal surgeons to visualize the primary surgical field on a high definition 3D screen, instead of looking through the eye-piece of a surgical microscope.

In some implementations, the auxiliary surgical field visualization system described herein may further include a processor and a non-transitory computer-readable medium, also referred to herein as "memory", accessible by the processor, wherein the non-transitory computer readable medium contains instructions executable by the processor for receiving, from the auxiliary surgical field camera, a signal that includes the image of the field of view of the secondary surgical field, and upon receiving the signal, sending the signal to a display.

Figure 3C:
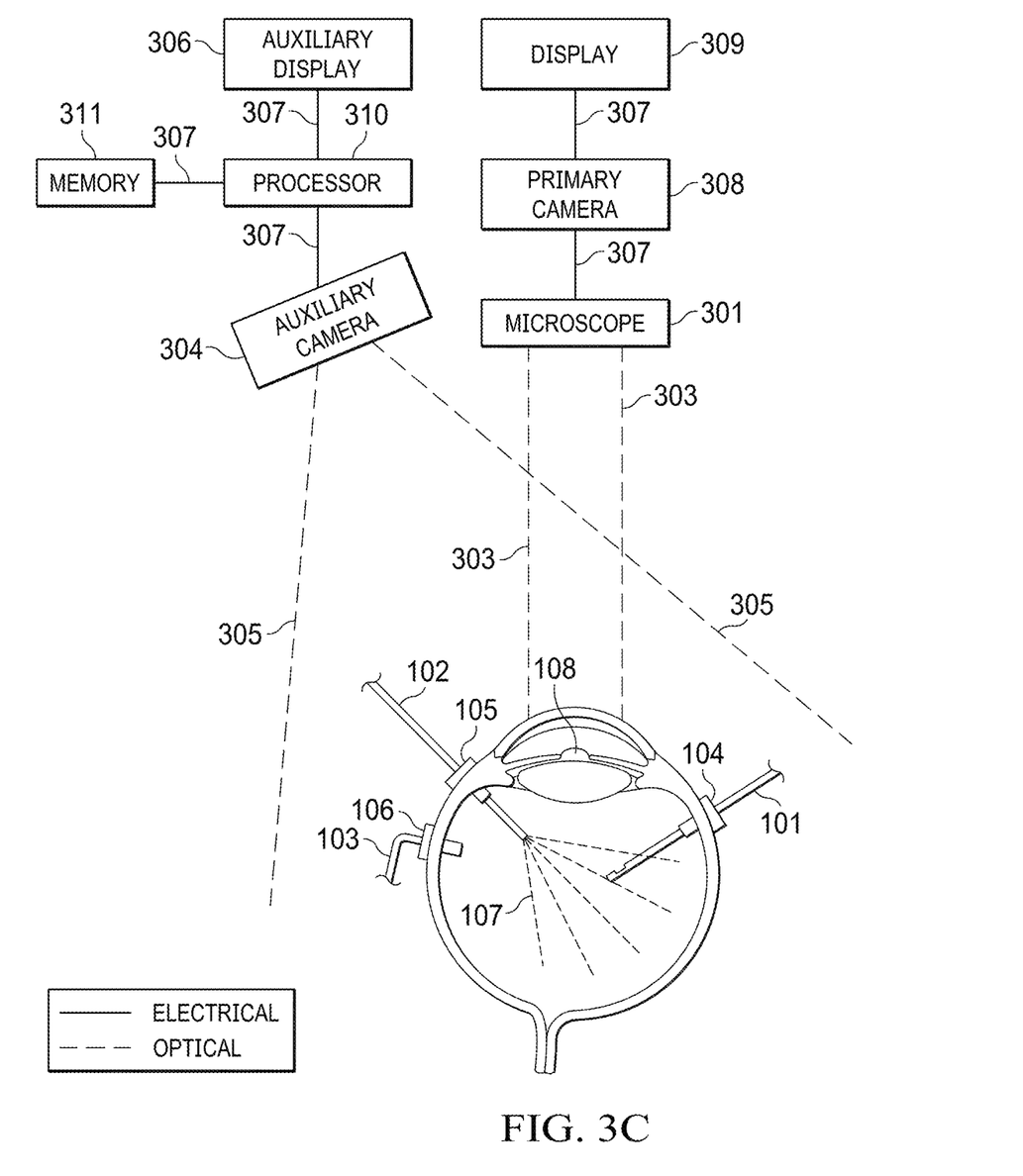
FIG. 3C is yet another schematic showing an exemplary exemplary auxiliary surgical field visualization system.

For example, FIG. 3C is a schematic showing another exemplary implementation of the auxiliary surgical field visualization system, including an auxiliary camera 304 configured for acquiring an image of a field of view of the secondary surgical field, shown by dashed lines 305 indicating exemplary boundaries of the field of view of the secondary surgical field. The exemplary implementation of the auxiliary surgical field visualization system includes a processor 310 and a memory 311 accessible by the processor 310, wherein the memory 311 contains instructions executable by the processor 310 for receiving, from the auxiliary surgical field camera 304, a signal that includes the image of the field of view of the secondary surgical field 305, and upon receiving the signal, sending the signal to the auxiliary display 306.

For example, the processor 310 may include any suitable computer having an operating system such as those of UNIX or UNIX-like operating system, a Windows family operating system, or another suitable operating system. The non-transitory computer-readable medium or memory 311 may encompass persistent and volatile media, fixed and removable media, and magnetic and semiconductor media, among others identifiable by persons of ordinary skill in the art. In addition, any suitable communication interface identifiable by skilled persons can be used as means for transmittal and receipt of electronic communication signals between the components of the auxiliary surgical field visualization system described herein.

Figure 3D:
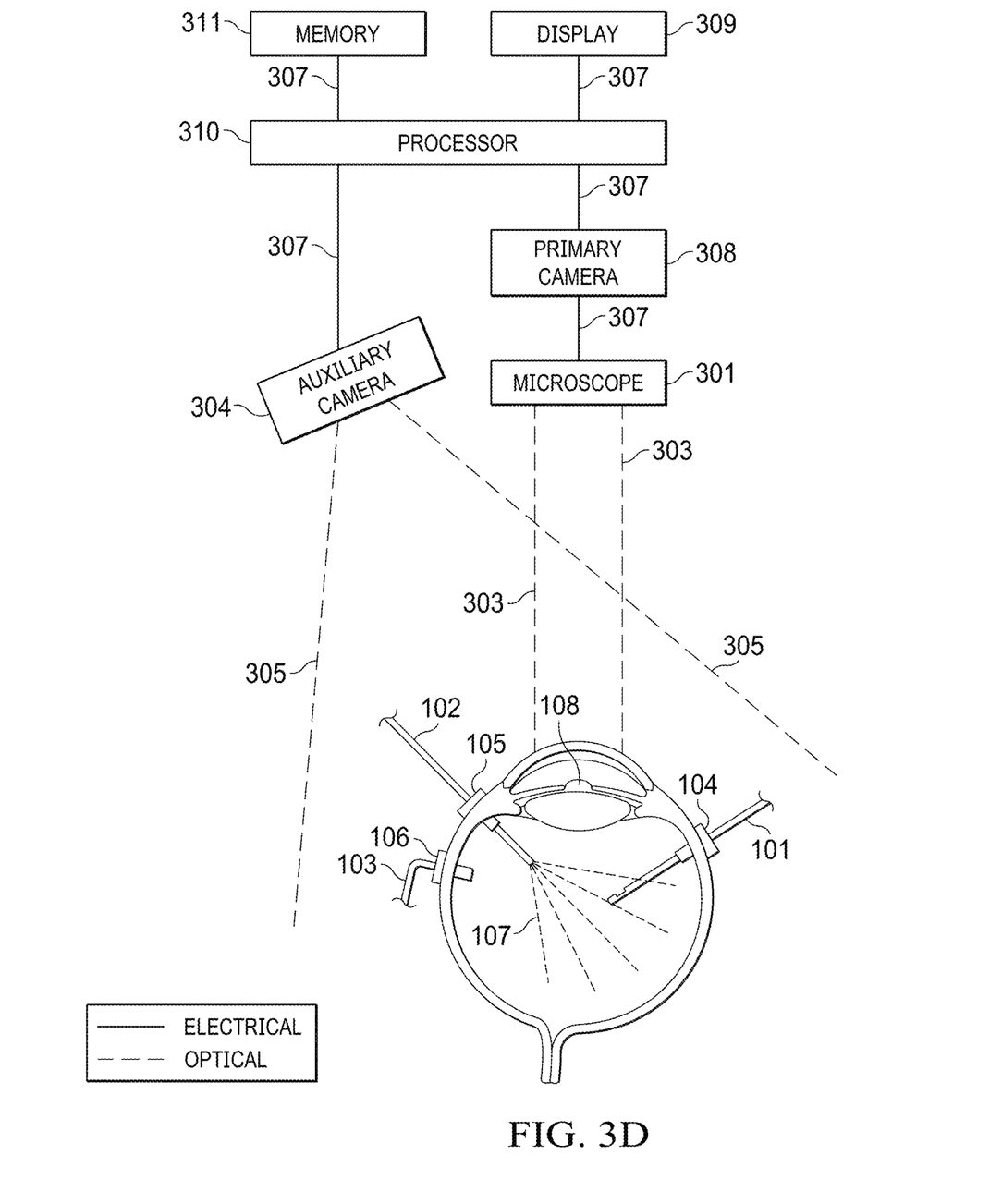
FIG. 3D is yet another schematic showing an exemplary exemplary auxiliary surgical field visualization system.

FIG. 3D is a schematic showing yet another exemplary implementation of the auxiliary surgical field visualization system. FIG. 3D shows the auxiliary camera 304 configured for acquiring an image of a field of view of the secondary surgical field, shown by dashed lines 305 indicating exemplary boundaries of the field of view of the secondary surgical field. The exemplary implementation of the auxiliary surgical field visualization system includes the processor 310 and the memory 311 accessible by the processor 310, wherein the memory 311 contains instructions executable by the processor 310 for receiving, from the auxiliary surgical field camera 304, a signal that includes the image of the field of view of the secondary surgical field 305, and upon receiving the signal, sending the signal to the display 309. In the exemplary implementation shown in FIG. 3D, the memory 311 also contains instructions executable by the processor 310 for receiving, from the primary surgical field camera 308 configured for acquiring an image of a field of view of a primary surgical field indicated by dashed lines 303 including an internal view of a patient's eye undergoing vitreoretinal surgery, a signal that includes the image of the field of view of the primary surgical field, and upon receiving the signal, sending the signal to the display 309. Accordingly, in various implementations, the image of the secondary surgical field may be displayed on an auxiliary display 306, such as shown in FIG. 3A, FIG. 3B, or FIG. 3C, or alternatively may be displayed on the same display 309 as the primary surgical field image, for example, either a 2D display, or a 3D display, such as those used in the NGENUITY® system. Accordingly, the exemplary auxiliary surgical field visualization system shown in FIG. 3D is configured in some implementations for displaying the image of the secondary surgical field and/or the primary surgical field. In some implementations, the auxiliary surgical field visualization system is configured for simultaneously displaying the images of the field of view of the secondary surgical field and the field of view of the primary surgical field.

In some implementations, the processor 310 and the memory 311 may be optional, in that the display 309 may be configured to either directly or indirectly receive, from the primary camera 308, a signal that contains an image of the primary surgical field, and to directly or indirectly receive, from the auxiliary camera 304, a signal that contains an image of the secondary surgical field.

In some implementations, the auxiliary surgical field visualization system described herein may further include a control panel or other suitable user interface accessible to a user, such as the surgeon or others in the surgical team, wherein the control panel is in electronic communication with the auxiliary surgical field visualization system and is configured to allow a user to select between the image of the primary surgical field of view and/or the secondary surgical field of view to be displayed on the display.

Figure 4:
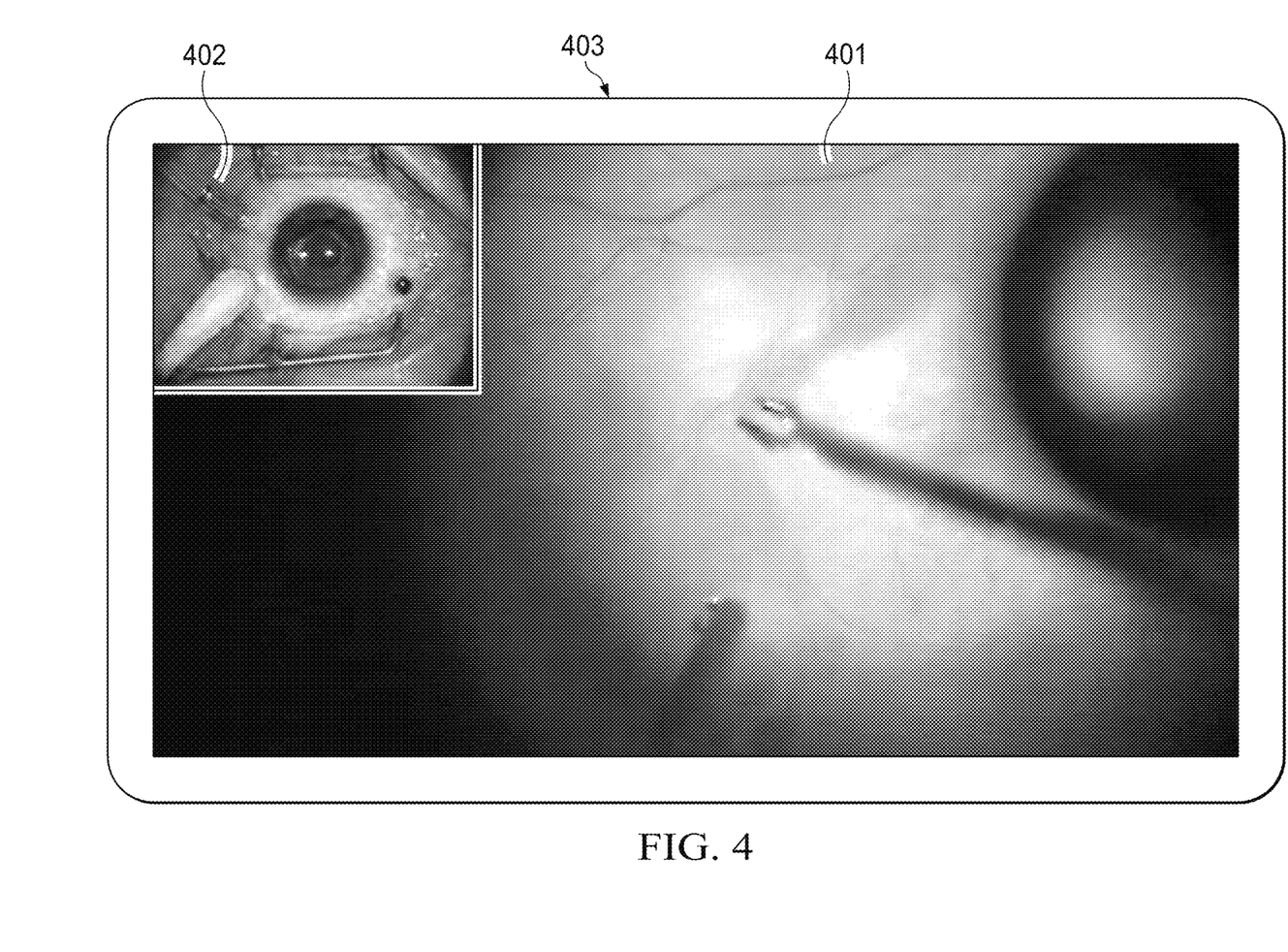
FIG. 4 is a schematic showing an example of a picture-in-picture view of an image captured by an auxiliary surgical field camera displayed together with an image of a view of an endoilluminated interior portion of an eye undergoing vitreoretinal surgery, as displayed on a display used as part of an NGENUITY® 3D Visualization System.

As shown in an exemplary schematic in FIG. 4, in some implementations, the image of the primary surgical field of view 401 and the image of the secondary surgical field of view 402 may be simultaneously displayed on the display 403 as a "picture-in-picture" arrangement. For example, the picture-in picture arrangement may be displayed on a display such as used in an NGENUITY® system. As would be understood by skilled persons, the term "picture-in-picture" as used herein refers to an arrangement wherein one image is displayed as an inset of another image. In various implementations, the image of the secondary surgical field may be displayed as an inset to the image of the primary surgical field, or vice-versa. In other implementations, the simultaneously displayed images of the primary surgical field and the secondary surgical field may be displayed side by side, or any other suitable arrangement on a single display. In various implementations, the primary surgical field image may be displayed approximately the same size, or larger or smaller than the secondary surgical field image.

Figure 5A:
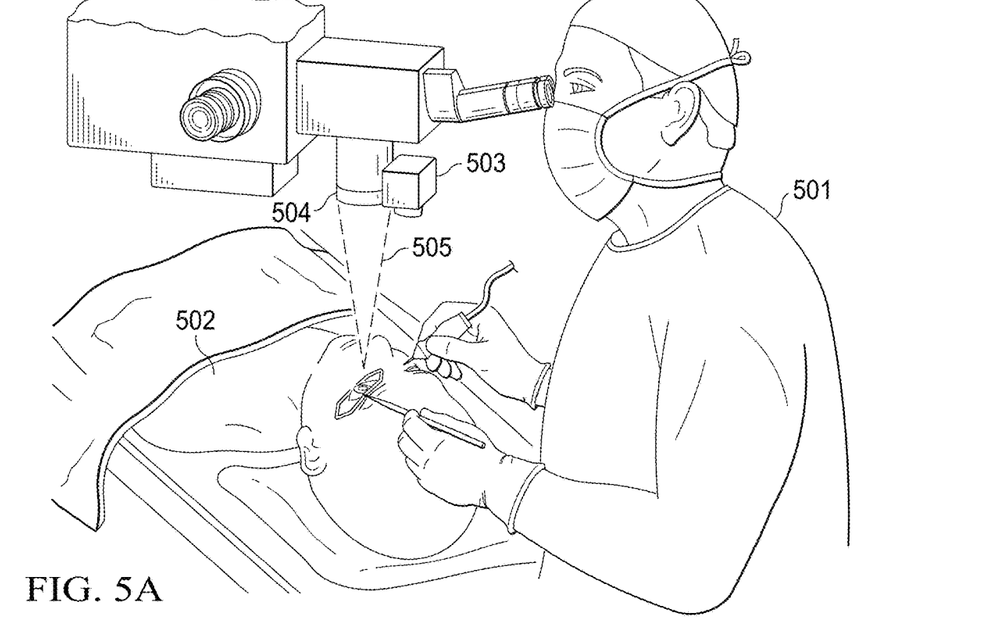
FIG. 5A is a schematic showing an exemplary attachment position of an auxiliary surgical field camera on the housing of a surgical microscope.
Figure 5B:
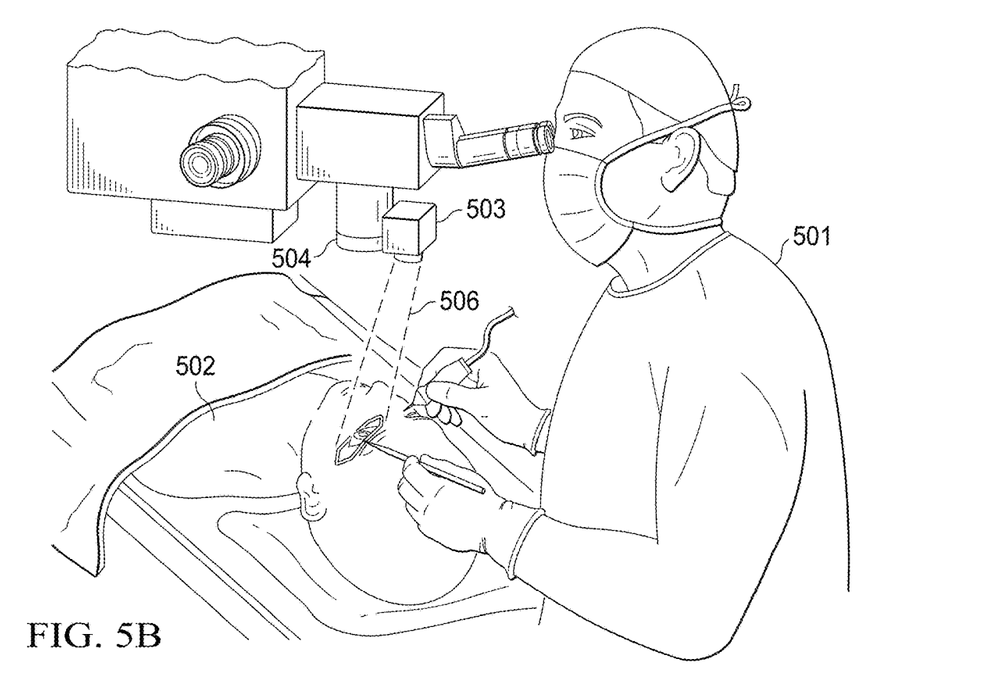
FIG. 5B is a schematic showing an exemplary attachment position of an auxiliary surgical field camera on the housing of a surgical microscope.

FIG. 5 is a schematic showing an exemplary location of an auxiliary camera included in the auxiliary surgical field visualization system as described herein. FIG. 5 shows an ophthalmic surgeon 501 operating on a patient 502. The auxiliary camera 503 is shown mounted, or attached, on the housing of a surgical microscope 504. Panel A shows an exemplary optical path of the field of view of the primary surgical field 505 as viewed through the surgical microscope 504, and Panel B shows an exemplary optical path of the field of view of the secondary surgical field 506 as viewed through the auxiliary camera 503. The auxiliary camera 503 may be located in different positions to that shown in FIG. 5. Other suitable positions allowing the auxiliary camera to capture an image of the secondary surgical field are identifiable by persons of ordinary skill in the art upon reading of the present disclosure.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. An auxiliary surgical field visualization system comprising:
   a primary surgical field camera configured for acquiring an image of a field of view of a primary surgical field comprising an internal view of a patient's eye undergoing vitreoretinal surgery, generating a first signal comprising the image of the field of view of the primary surgical field, and displaying the image of the field of view of the primary surgical field;
   an auxiliary surgical field camera comprising a low light camera and an electronic photosensor configured for acquiring an image of a field of view of a secondary surgical field and generating an additional signal comprising the field of view of the secondary surgical field, wherein the secondary surgical field comprises the exterior of a patient's eye undergoing vitreoretinal surgery and one or more surgical components in the secondary surgical field selected from a trocar cannula, an infusion line, a needle holder, an indentor, a muscle hook, an instrument tip prior to insertion trough a trocar cannula, a flexible iris retractor, a direct or indirect contact lens, and a needle and suture; and
   a display in electronic communication with the primary surgical field camera and the auxiliary surgical field camera, wherein the display is configured to:
      receive the first signal and displaying the image of the field of view of the primary surgical field; and
      receive the additional signal and display the image of the field of view of the secondary surgical field, and wherein the image of the field of view of the secondary surgical field is simultaneously displayed as an overlay on top of the image of the field of view of the primary surgical field and is viewable in low light conditions.

2. The auxiliary surgical field visualization system of claim 1, wherein the eye is illuminated using endoillumination.

3. The auxiliary surgical field visualization system of claim 1, wherein the secondary surgical field has a light intensity of less than 2000 lux.

4. The auxiliary surgical field visualization system of claim 1, wherein the area of the field of view of the secondary surgical field is between about 1 cm2 and 36 cm2.

5. The auxiliary surgical field visualization system of claim 1, wherein the image is a real-time image.

6. The auxiliary surgical field visualization system of claim 1, wherein the display is a standard definition (SD) display, a high definition (HD) display, a cathode ray tube (CRT) display, a projection screen display, a liquid crystal display (LCD), an organic light emitting diode (OLED) display, a plasma display, a light emitting diodes (LED) display, or a 3-dimensional (3D) display.

7. The auxiliary surgical field visualization system of claim 1, further comprising:
   a processor; and
   a non-transitory computer-readable medium accessible by the processor, wherein the non-transitory computer readable medium contains instructions executable by the processor for:
   receiving, from the auxiliary surgical field camera, the additional signal comprising the image of the field of view of the secondary surgical field, and upon receiving the additional signal, sending the additional signal to the display.

8. The auxiliary surgical field visualization system of claim 7, wherein the non-transitory computer-readable medium further comprises instructions executable by the processor for:
   receiving, from the primary surgical field camera configured for acquiring the image of a field of view of the primary surgical field comprising the internal view of a patient's eye undergoing vitreoretinal surgery, the first signal comprising the image of the field of view of the primary surgical field, and upon receiving the first signal, sending the first signal to the display.

9. The auxiliary surgical field visualization system of claim 1, wherein the auxiliary surgical field visualization system allows visualization on a display of one or more secondary surgical manipulations, wherein the secondary surgical manipulations are directed to a site on or adjacent to the exterior surface of the eye.

10. The auxiliary surgical field visualization system of claim 9, wherein the secondary surgical manipulations comprise one or more manipulations selected from inserting an instrument into the eye through a trocar cannula, suturing an exterior surface of the eye, placing a trocar cannula, removing a trocar cannula, inspecting a function of a surgical component, retrieving a foreign body, placing indentors or muscle hooks, using cryo-probes, placing scleral buckles and encircling bands, and placing a direct or an indirect contact lens.

11. The auxiliary surgical field visualization system of claim 1, wherein the display is viewable by a plurality of individuals.

* * * * *